(12) United States Patent  
Margalith

(10) Patent No.: US 8,687,055 B2  
(45) Date of Patent: Apr. 1, 2014

(54) SPECTRAL IMAGING OF MOVING OBJECTS WITH A STARE DOWN CAMERA

(76) Inventor: Eli Margalith, Solana Beach, CA (US)

(*) Notice: Subject to any disclaimer, the term of this patent is extended or adjusted under 35 U.S.C. 154(b) by 745 days.

(21) Appl. No.: 12/661,369

(22) Filed: Mar. 16, 2010

(65) Prior Publication Data

US 2011/0228116 A1 Sep. 22, 2011

(51) Int. Cl.
*G01J 3/00* (2006.01)

(52) U.S. Cl.
USPC ............... 348/91; 348/92; 356/300; 356/317; 356/318

(58) Field of Classification Search
None
See application file for complete search history.

(56) References Cited

U.S. PATENT DOCUMENTS

| | | | |
|---|---|---|---|
| 5,450,125 A * | 9/1995 | Ulich et al. | 348/31 |
| 2005/0213089 A1* | 9/2005 | Margalith et al. | 356/300 |
| 2006/0262180 A1* | 11/2006 | Robbins | 347/257 |
| 2006/0282223 A1* | 12/2006 | Lewis et al. | 702/19 |
| 2007/0057211 A1* | 3/2007 | Bahlman et al. | 250/584 |

* cited by examiner

*Primary Examiner* — Twyler Haskins
*Assistant Examiner* — Dwight C Tejano
(74) *Attorney, Agent, or Firm* — John R. Ross; John R. Ross, III

(57) ABSTRACT

A spectral imaging system for collecting spectral information of a two dimensional heterogeneous objects while in motion relative to the imaging system without the use of a spectrograph, filters or any dispersive optics. The system includes a pulsed light source tunable in wavelength for producing short pulses of wavelength tuned light at a plurality of selected narrow band wavelengths within a spectral range and one or more optical components for conveying or directing the short pulses of light to a two dimensional region that is substantially stationary with respect to the imaging system and through which the two dimensional target is moving. The system also includes a many pixel camera synchronized with the tunable pulsed light source. The camera is adapted to detect light in the selected narrow band wavelengths produced by the tunable pulsed light source and reflected from or transmitted through the two dimensional target in motion relative to the imaging system and to provide image frame information with each frame at a defined wavelength band. A processor processes information from said tunable light source and said camera and to produce multi-spectral images of the target.

4 Claims, 3 Drawing Sheets

SPECTRAL IMAGING OF MOVING OBJECTS WITH A STARE DOWN CAMERA

The present invention relates to multi-spectral imaging systems and in particular to such systems where the target region is moving with respect to the camera or the camera is moving with respect to the target region.

BACKGROUND OF THE INVENTION

Spectroscopy

Spectroscopy is a technique for identifying and analyzing substances through the spectrum emitted from or absorbed by them. The technique is often used to analyze the chemical composition and physical properties of objects, and is being utilized in a range of applications from scientific research to food inspection. The spectral information allows checking source materials, process intermediates, and characterization and validation of finished products. The technique is based on measuring the optical characteristics of an object, such as reflection, absorption, or transmission, as a function of wavelength. Since each material has a characteristic optical signature the information collected by the spectrometer can be used to identify the composition of the object. The technique has applications in chemistry, biology, medicine, pharmacy, agriculture, food industry, and in production of consumer products.

A typical spectrometer measures the light intensity as a function of wavelength reflected from or transmitted through an object. The recorded data represents the averaged spectrum of the object over the area viewed by the spectrometer. This method works well for homogeneous objects, however, if the object is heterogeneous it may be difficult to identify and quantify the compounds it is made of, and there is no information about their distribution within the object. To obtain data that identifies the chemical content of a heterogeneous target requires taking multiple spectra across the target, with a spot size defined by the required resolution. Depending on the target size and the resolution, generating such information by scanning can be very tedious and time consuming.

Spectral Imaging

Spectral imaging (also known as chemical imaging, multi-spectral imaging or hyper-spectral imaging) refers to obtaining spectral information with high spatial resolution from a 2-D target. The difference between multi-spectral imaging and hyper-spectral imaging is usually made on the basis of the number of spectral bands in the image. In order to acquire this information the image of the target is recorded at numerous wavelengths generating a 3-D data set, whereas two dimensions of the data are the physical dimensions of the target (e.g. width and length) and the third dimension provides the wavelength information associated with each point on the target. FIG. 3 provides a graphical presentation of a hyper-spectral cube. The cube has three dimensions as presented in FIG. 3. The physical dimensions of the target X and Y and the third dimension is the wavelength $\lambda$

Existing Spectral Imaging Systems

The multi-spectral and hyper-spectral cubes can be collected in three basic methods:
1. Point scanning; in which a wavelength spectrum at a small area on the target, represented by a point coordinate ($X_i, Y_i$), of the object is recorded, and the two physical dimensions are obtained by scanning the spot over the entire object. Typically, the spot is illuminated by a broadband light source and the reflected light is collected by a spectrograph. The spectrograph records the reflectivity as a function of wavelength at the spot. The hyper-spectral-cube of the entire object is collected by scanning the spot over the object. The process is very slow, which limits the use of instruments based on this technique to R&D applications and laboratory environment.
2. Line scanning (also known as push-broom); in which the spectral information along a line on the target is recorded. The hyper-spectral cube is obtained by scanning the line across the other dimension of the object. In this technique, the object under investigation may be illuminated by a "strip" of light generated by a broadband light source. The length of the strip is defined by the width of the object. The reflected light from the strip is analyzed by an imaging spectrograph. A camera with a 2-D array (e.g. CCD, or FPA), records the reflectivity as a function of wavelength for each point along the strip. The data collection is much faster than that of a point scan since an entire line along the object in analyzed simultaneously. However, the cost of such instrument is higher since the simple spectrograph with a line array detector used in the point-scan technique is replaced by an imaging spectrograph with a 2-D camera.

The push-broom technique is typically used for analyzing objects that are moving across the field of view of a camera having a one-dimensional field-of-view perpendicular to the direction of travel. The technique is implemented in airborne and space born applications in which the camera is mounted on an airplane or a satellite, looking down at a narrow region perpendicular to the direction of travel. Light reflected from these regions is collected through a spectrometer by a two dimensional detector such that the spectrum of each narrow "one dimensional" region under the flight path is recorded. These targets can be agriculture related; e.g. health of crops; type of crops, or defense related; searching for enemy activities based on spectral signatures of people or vehicles. This technique has been used in industrial applications in which objects are moving on a conveyor belt. The hyper-spectral camera can inspect raw materials, finished goods, or sort waste and disposable material.

The push-broom technique can also be used to analyze stationary objects. In this case the illumination is directed to the target with a mirror that scans the strip of light across the object and the reflected light is scanned into the spectrograph.
3. Stare-down; in this case a two-dimensional object is illuminated and the reflected light is recorded by a two dimensional camera. Early stare-down instruments utilized a broadband light as the illumination source and the reflected light from the object passed through narrow-band transmission filters before reaching the camera. The reflected spectra were collected by taking pictures of the object while changing filters, or changing the filter's wavelength transmission (such as with a liquid crystal tunable filter; LCTF). In an alternative technique, a tunable light source such as an optical parametric oscillator (OPO) that emits a spectrally narrow light is used to illuminate the object one wavelength at a time. The camera sensor is an array of detectors, also known as pixels, typically in a shape of a square. The light reflected of the target is recorded by the detector array and constructed into an image by the camera electronics and software. The target can be presented as a matrix of virtual squares, each corresponding to a pixel of the camera. The ratio between the size of the target pixels and the camera pixels is defined by the choice of optics in front of the camera, and is known as magnification.

Optical Parametric Oscillators

Optical Parametric Oscillators are optical devices that incorporate non-linear crystal(s) in an optical resonator. The OPO can convert a fixed output wavelength of a laser (known as pump) to different wavelengths which can vary over a wide spectral range.

The OPO wavelength is determined by the choice of the non-linear crystal, the pump wavelength, the temperature of the crystal, and the orientation of the crystal with respect to the pump laser beam. Wide wavelength tuning is achieved by varying the angle between the optical axis of the crystal and the direction of the pump beam (angle tuning). The spectral resolution of the instrument is defined by the OPO linewidth. The linewidth of the OPO beam is primarily a function of the crystal material, the crystal orientation, and the pump wavelength, e.g. a relatively narrow linewidth of less than 10 cm$^{-1}$ is obtained over a wavelength range of 410 nm to 2400 nm from a OPO incorporating a BBO crystal in a type II orientation, pumped by a laser beam at 355 nm.

OPO are very well known and have been commercially available for many years.

Prior Art Spectral Imagers

Spectral imaging, and specifically near infrared (NIR) imaging, is well documented in the literature and in numerous patents. U.S. Pat. No. 5,276,548 presents an NIR imaging device (a microscope) using a broadband light source and tunable filters. U.S. Pat. No. 6,259,160 describes a spectral imaging system utilizing a LED illuminator which produces illumination of pure wavelengths or a mixture of pure wavelengths simultaneously. U.S. Pat. No. 7,420,679 describes a method and apparatus for obtaining a multimode hyper-spectral image of samples for wide field spectral analysis utilizing multiple filters and lenses. All of the above patents are incorporated herein by reference.

Various spectral imaging products are commercially available; e.g. SyNIRgi, by Malvern, the Nuance FX by Cambridge Research Inc., Condor by ChemImage, and HySPEC by OPOTEK.

Applicants' Stare-Down Multi-Spectral Imager

The prior art also includes a U.S. Pat. No. 7,233,392, issued to Applicant and another in 2007 for making multi-spectral images using a OPO as the light source. That patent is incorporated herein by reference. This patent describes a "stare-down" type of multi-spectral imagers. The background section of that patent discusses other types of stare-down multi-spectral imagers. These imagers typically utilize wavelength filters or grating type spectrometers to separate reflected emitted or transmitted light into spectral components. The OPO light source described in detail in that patent could be tuned over a wide range of wavelengths. FIG. 2 is a drawing from that patent providing a good description of the invention described in that patent. A target 4 is illuminated with a laser pumped OPO 2. The wavelength could be scanned between 410 nm to 2400 nm. The system included laser control electronics 3, laser power supply 1 laser head 1A, OPO crystal 2, tuning control 2A, computer processor 30 and camera with electronics 7. Target 4 was illuminated through optical fiber 32 and reflections 21 from the target were recorded by camera system 7 to produce a multi-spectral image of target 4. That patent refers to preferred off-the-shelf cameras with a large number of pixels such as 640 times 512 for the two-dimensional spatial image. The third dimension is provided by the OPO system with wavelengths ranging from 410 nm to 2400 nm which could be controlled to a precision of a "fraction of a nanometer to a few nanometers depending on the wavelength". The net result was a "hyper-spectral cube", an example of which was shown in FIG. 8 of that patent and is presented here as FIG. 3. As indicated in the above described patent the use of OPO systems to obtain three dimensional (including a wavelength dimension) images of a target provided substantial advantages over the prior art stare-down multi-spectral imaging techniques.

The Need

The prior art related to spectral imaging of moving targets is limited to "push-broom" or "line-scanning" methods. These methods require the use of a spectrograph or multiple filter that limit the performance of such systems. What is needed is a stare-down spectral imaging system for imaging targets moving with respect to the imaging system.

SUMMARY OF THE INVENTION

The present invention provides a spectral imaging system for collecting spectral information of a two dimensional target in motion relative to the imaging system. The system is substantially different from the push-broom technique described in the background section as it does not incorporate a spectrograph or any other wavelength dispersion elements. The main advantage is provided by the use of a tunable light source (OPO) to illuminate the target. The system provides the means to use a stare-down configuration to image moving target with all the advantages described in detail in U.S. Pat. No. 7,233,392, The system includes a pulsed light source tunable in wavelength for producing short pulses of wavelength tuned light at a plurality of selected narrow band wavelengths within a spectral range and one or more optical components for conveying or directing the short pulses of light to a two dimensional region that is stationary with respect to the imaging system and through which the two dimensional target is moving. The system also includes a many pixel camera synchronized with the tunable pulsed light source. The camera is adapted to detect light in the selected narrow band wavelengths produced by the tunable pulsed light source and reflected from or transmitted through the two dimensional target in motion relative to the imaging system and to provide image frame information with each frame at a defined wavelength band. A processor processes information from said tunable light source and said camera and to produce multi-spectral images of the target.

In preferred embodiments the system in a stare-down configuration without the use of a spectrograph, dispersive optical elements, or filters. In this preferred embodiments a stationary tunable optical parametric oscillator (OPO) provides the illumination of a target region passing below the OPO. Preferably, the pixel array of the camera is a near infrared focal plane array (FPA). A processor converts information collected by the FPA into hyper-spectral image cubes. These images cubes identify optical parameters such as transmission, or reflectivity, of the target region. The present invention can be applied in spectral regions other than near infrared depending on the application requirements. These spectral ranges include wavelengths from ultraviolet to infrared for a variety of applications including metrology, agriculture, life sciences, food industry, and in the pharmaceutical industry.

In preferred embodiments the quality of the data acquired at each wavelength in a single frame is high enough to enable the analysis of the object without the need to take multiple frames at the same wavelength. Applicant has shown with his preferred embodiment that using the OPO as the illumination source, the quality of the data acquired in a single frame is as good as data that is obtained by averaging multiple frames.

DETAILED DESCRIPTION OF PREFERRED EMBODIMENTS

First Preferred Embodiment

Figure 1:
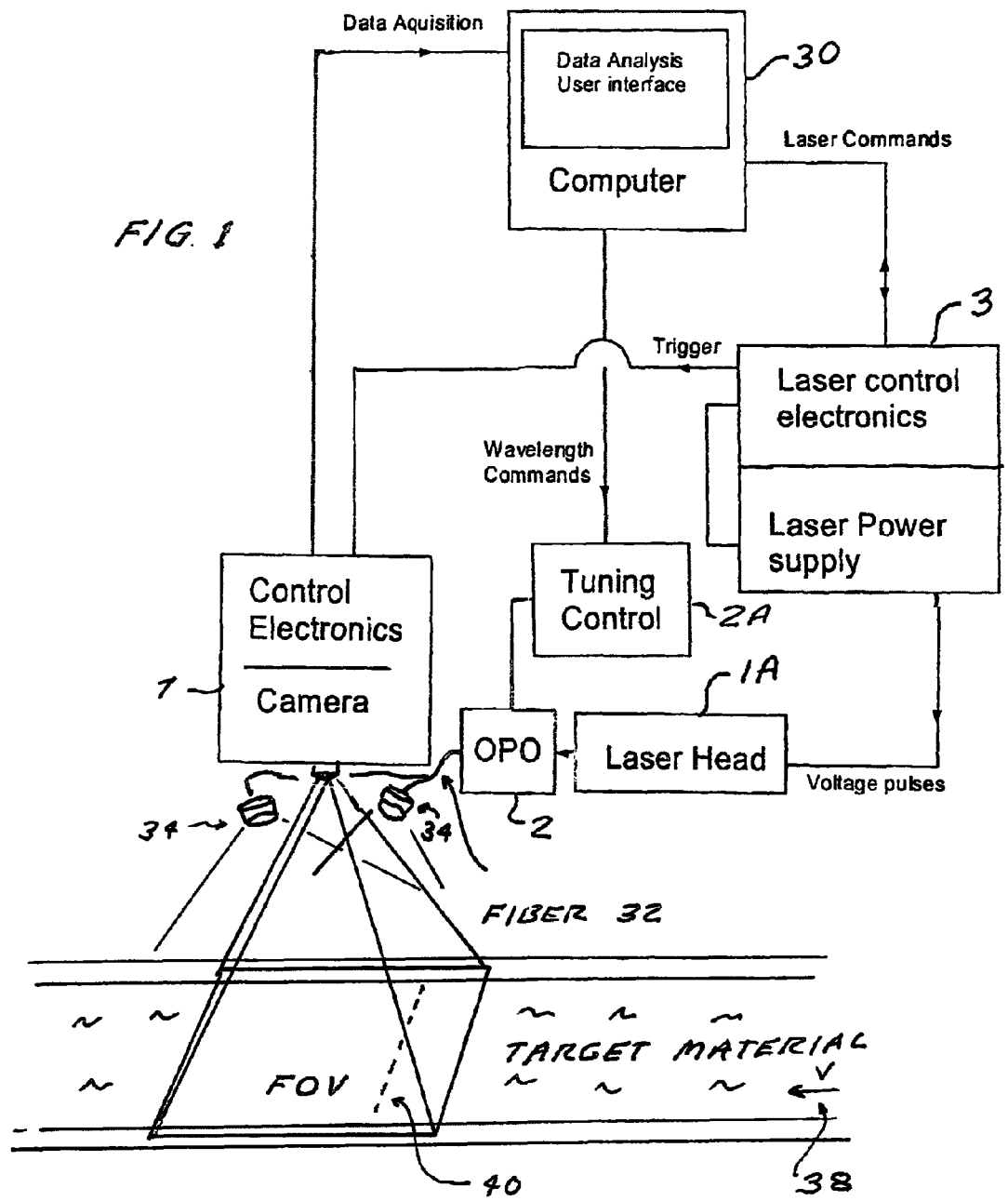
FIG. 1 is a drawing showing important features of a preferred embodiment of the present invention.
Figure 2:
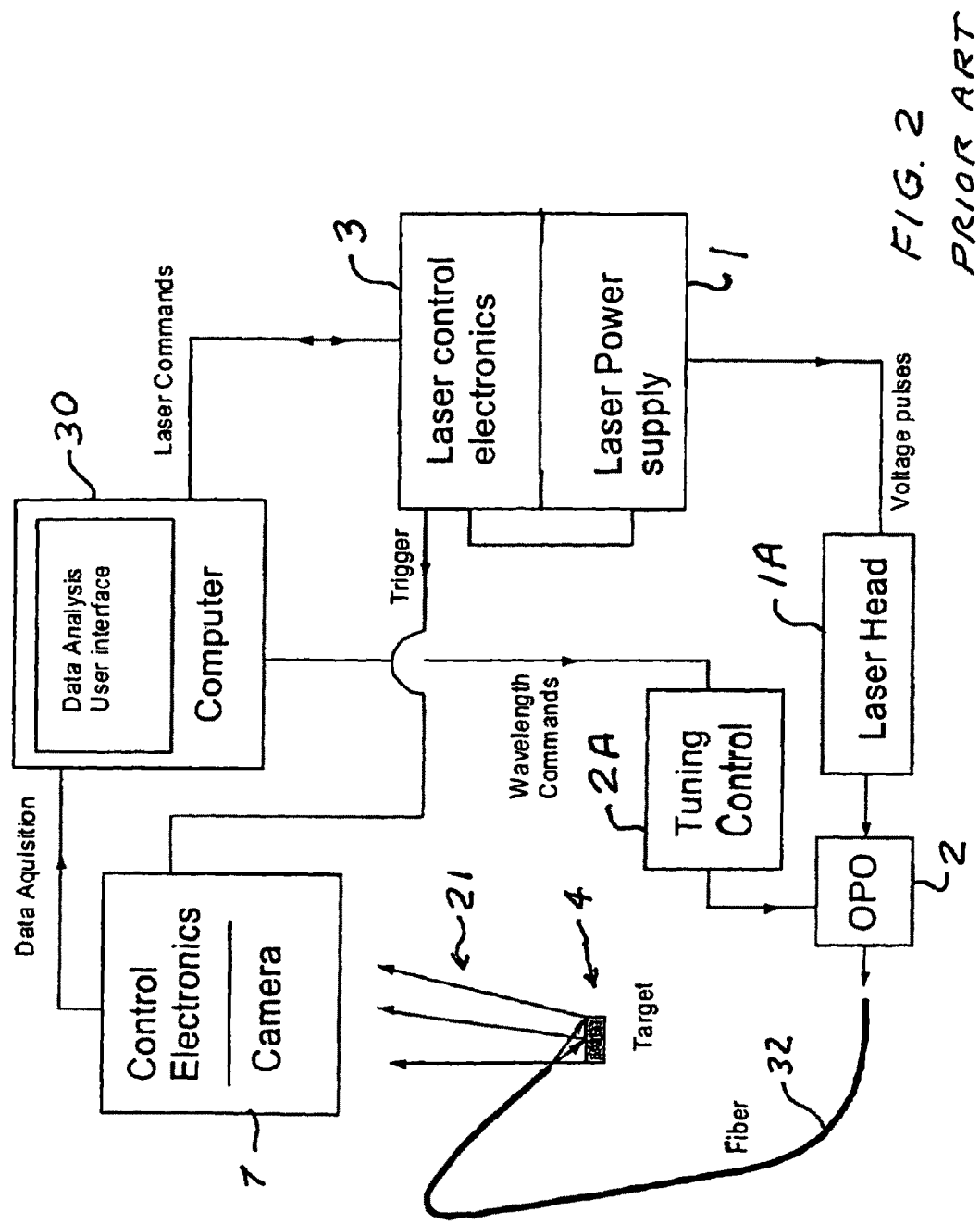
FIG. 2 is a drawing of prior art spectral imaging device having a tunable illumination source.
Figure 3:
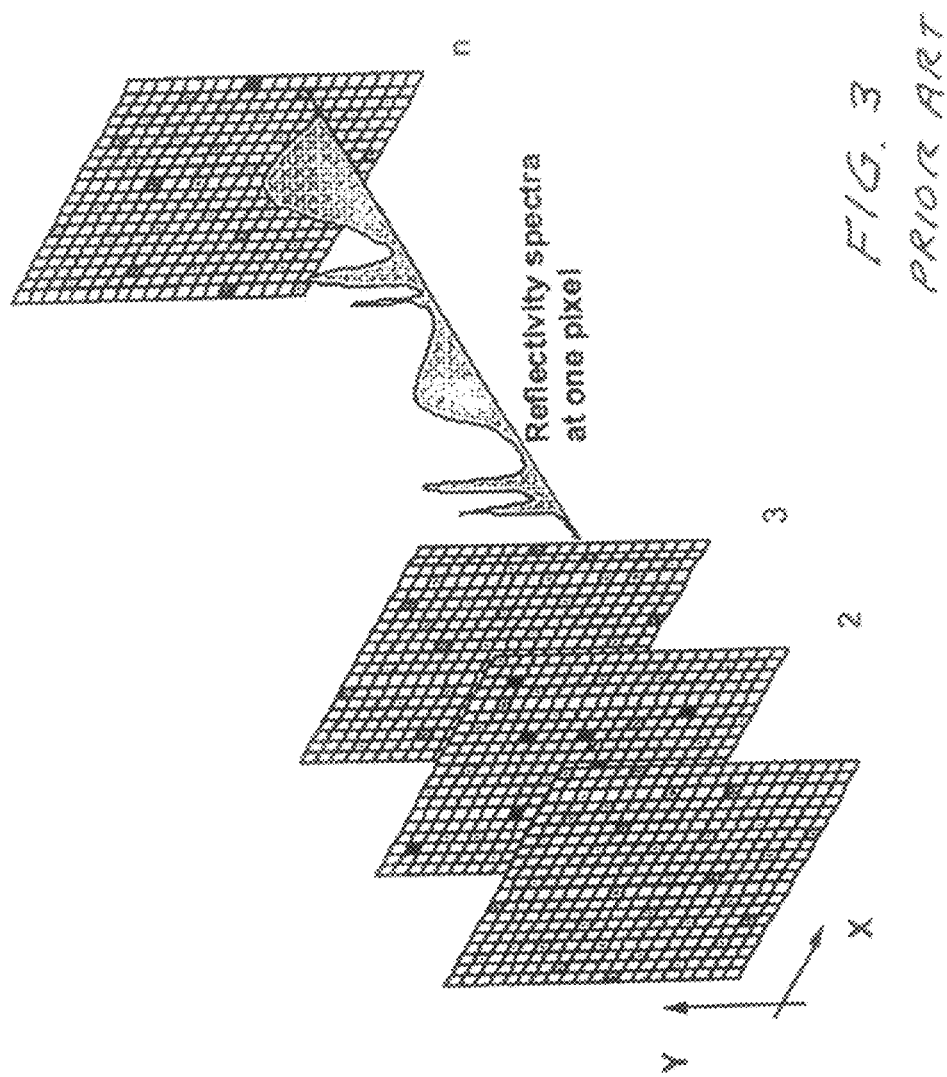
FIG. 3 shows a presentation of hyper-spectral image data.

FIG. 1 presents a typical setup of a stare-down spectral imaging system. Camera 7 collects light directed by optical fibers 32 and lens system 34 at a portion of target material 36 passing through the field of view (FOV) of the camera. A pixel array of camera 7 defines an array of virtual pixels in the camera's FOV. The magnification can be controlled by selecting the appropriate camera lens.

The objects to be analyzed are moving through a target region defined by the camera's FOV in the direction indicated by the arrow 38 at a speed V. The target region's length is defined as the FOV in the direction of motion and the target region's width is defined as the FOV perpendicular to the motion direction.

The light from the OPO is delivered through optical fibers 32 to completely cover the target area. The fibers are terminated with lens systems 34 that include lenses and/or diffusers. The output of the OPO preferably is divided into several separate fiber assemblies in order to optimize the illumination uniformity and decrease the effect of speckle. The reflected light from the target is collected by camera 7. The light is generated and collected in extremely short pulses, on the order of a few nanoseconds, such that the pictures are not "blurred" by the motion of the target material.

To understand the principle of operation and the data collection method, the reader should consider a narrow strip in the target region, which corresponds to a column 40 (one pixel wide) of virtual pixels. The virtual strip "moves" with the objects in the same direction and speed. As the strip moves across the target the laser is firing and the wavelength is scanned such that each pulse is tuned to a different wavelength. The number of "strips" in the FOV is equal the length of the FOV in the direction of motion divided by the width of the strip. In each frame, the camera records the entire FOV. The camera is synchronized with the laser to record a frame for each laser pulse. The actual wavelength is recorded for each frame by a build-in, calibrated spectrometer. The laser firing is synchronized with the motion of the target such that the time interval between pulses is identical to the time it takes to the objects to move a distance equal to the width of the strip. In this case, every time the strip is moved by a distance equal to its width, it will be illuminated at a different wavelength. When the strip completes its "trip" across the target area the objects within the strip will be exposed to a set of discrete wavelengths. The reflected light from the objects within the strip will be recorded by the camera's pixels that correspond to the virtual pixels of the strip at the time of the laser pulse. The data acquisition software tracks the light reflected from each strip as it passes through the FOV such that the spectrum of each pixel on each strip is reconstructed to provide the spectral information of the moving object.

Spectral Resolution

The spectral resolution of the instrument is defined as the wavelength spacing between two consecutive frames. The spectral resolution can be controlled by varying the either the pulse repetition rate of the laser or the rate at which the wavelength tuning mechanism is changing wavelength.

The system parameters are defined as follows:

Np=number of pixels in the FOV in the motion direction
Nps=number of pixels in the strip's width
Ns=number of strips in the field of view
PIX=Virtual pixel dimensions
PRR=pulse repletion rate of the laser
V=target speed (conveyor belt speed)
$\Delta\lambda$=Wavelength range
F=number of frames (spectral bands in the spectral data)
SR=Spectral resolution
Ws=Strip width The strip width can be as narrow as the width of a single virtual pixel on the target as suggested above or the strip can be wider. The system parameters are adjusted such that each strip is exposed only once to each wavelength as it travels across the target area. Therefore, the number of pulses that a strip is exposed to is equal to number strips in the target area, which is also equal to the number of data points (#F) in the collected spectral data.

$$\#F = Ns = \frac{Np}{Nps}$$

The spectral resolution is equal to the total wavelength range scanned by the OPO divided by the number of the collected data points.

$$SR = \frac{\Delta\lambda}{\#F}$$

For a desired number of frames #F the required speed is the product of the pulse repetition rate and the width of the strip $$V = Ws*PRR = Nps*PIX*PRR$$

For example, let us assume that:

The camera array is 320×256 pixels and it is oriented such that the 256 pixels are along the direction of motion.
The strip is one pixel wide.
The virtual pixel size on the target is 1 mm.
The laser pulse repetition rate is 20 Hz.
The wavelength range is 1000~1700 nm
Therefore, the number of strips in the field of view, Ns, is 256 and the required motion speed will be:

$$V = PIX [mm]*PRR[1/sec] = 1*20 = 20 [mm/sec]$$

The spectral resolution will be:

$$SR = \frac{(1700-1000)}{256} = 2.73 \text{ nm}$$

The spectral resolution is inversely proportional to the target speed; therefore, by reducing the spectral resolution by a factor of 2 to 5.76 nm the target speed can be increased by a factor of 2 to 40 mm/sec. In this case the virtual strip will be 2 pixels wide. However, the spatial resolution, which is defined by the dimensions of a single virtual pixel, will remain unchanged.

For a given speed and pulse repetition rate, the spectral resolution (SR) and the spatial resolution (PIX) are inversely related, as can be seen from the following equation $$V = \left(\frac{PRR*Np}{\Delta\lambda}\right)*PIX*SR$$

The parameters will differ based on the application. Some applications require high spatial resolution, whereas speed may be the most important parameter for others. Compounds that have very well defined spectral features may be identified by a few wavelengths, which will allow for higher speed and higher spatial resolution. Basically, the data generated by this technique is similar to the data collected in the push-broom technique, but without the use of a spectrograph. The main advantages are higher light throughput, better spectral resolution, and higher flexibility in meeting various requirements, e.g. the spectral resolution can be varied to meet the applications' needs.

Wavelength Tuning

The OPO has to scan over the entire wavelength range in the same time that it takes for an object to travel across the target area. The time to complete the scan is provided by the following equation:

$$T = \frac{Np*PIX}{V}$$

The wavelength scan has to be repeated in order for each strip to be illuminated only once by the same wavelength. That means that if the wavelength scan starts with the shortest wavelength and ends with the longest one in the range, the wavelength has to "jump" at the end of the scan from the longest wavelength to the shortest one in the time between two consecutive pulses.

One option to enable such a quick wavelength change is to incorporate two OPO units pumped by a single laser. In this case, while one OPO is scanning forward and illuminating the target, the other OPO is retreating to the start wavelength in preparation for the next scan. Switching between the two OPOs can be easily accomplished using an electro-optics device (such as a Pockels Cell) in combination with a polarizer. The switching can be completed in a time of less than a millisecond.

Another option is to cycle the wavelength tuning and scan up and down the wavelength range. However, in this case the data collection speed will be slower by a factor of 2 and each strip will be illuminated twice at each wavelength.

Calibration

The system has to be well calibrated in order to generate useful data. The calibration methods are identical to the calibrations that are already implemented in a commercial stare-down spectral imaging instruments such as the HySPEC model available from Opotek, Inc. with offices in Carlsbad, Calif. The calibration has to provide reference information that will enable correction for the following parameters:
1. Non uniformities in the camera response,
2. Non uniformities in the illumination field and
3. Variation in the illumination intensity from frame to frame The calibration process can be performed in two steps; the camera and the illumination non-uniformities can be recorded prior to using the system, while the variations in the illumination intensities in each frame are corrected in real time when the system is used.

Pre-Run Calibration

The first step in the calibration is to record the camera's response without illumination. A simple way to accomplish it is by placing a cap over the lens. The response to "dark" is the inherent noise of the camera and is different for each detector in the array. The "dark" response is subtracted from the actual response of each detector. This calibration has to be done only once.

Each detector in the camera array has different response to light intensity which has to be accounted for. The response may change as a function of the wavelength of the light. In addition, the illumination intensity on the target area is not uniform and varies from point to point. The non-uniformity in the intensity is a function of the illumination method, which includes the light source and the optical delivery system.

The variations of the individual pixel response to the actual illumination field are recorded before the system is put to use and are stored in the system software as a calibration matrix. The calibration process is very simple. A target with a uniform and calibrated reflectance is placed in the target area. The reflectivity of the calibrated standard as a function of wavelength is known, and is typically high, on the order of 99%. The system is turned on and the wavelength is scanned over the entire range with small steps. The system can be set to record multiple frames at each wavelength to minimize the Signal to Noise. The recorded data provides the response of each pixel to the actual illumination field at the specific setting. The calibration data is used during the data processing to "remove" the effects of the non-uniformities from the data. As long as the setting is not changed there is no need to repeat the calibration.

Real Time Calibration

The illumination field will remain unchanged as long as there are no physical changes to the system configuration. However, the light intensity may vary from frame to frame. In order to correct for these fluctuation a small reflectance standard (typically with 99% reflectivity) is placed in the field of view of the camera, on a stationary section such that it does not interfere with the motion of the objects or the conveyor belt, as presented in FIG. 1. The signal reflected from the standard is used to "normalize" the collected data. In addition, 3 more standard reflectance targets, with different reflectance values are placed in the FOV of the camera, on a section stationary with respect to camera 7. These reflectance targets could have reflectance values of for example of 99%, 60%, 40% and 2%. The signal reflected from these targets is recorded and used for fine correction of any non-linearity of the camera's response.

Implementing the above calibration techniques, assures that the signal recorded by each detector in the camera array is calibrated and normalized at each frame to represent the reflectivity of the target independent of the variations in the illumination field, camera nom-uniformities, and fluctuations of the illumination intensities.

Variations

The above described preferred embodiment is only one of many ways this invention can be practiced. Persons skilled in the art will recognize many variations are possible within the scope of the invention. Some of these variations are suggested below.

Transmission

The above described preferred embodiment is based on light reflected from a target region. Similar systems can be configured to measure other optical parameters such as transmission, fluorescence etc. The instrument can be configured to obtain spectral imaging of transmitted light through the target. Images of transmitted light can provide integrated information of the material composition within the target in the volume acquired by each sensor in the array. The basic components are the same as in FIG. 1 except that the light from the OPO is directed to one side of the target whereas the camera is placed on the opposite side. The OPO can be delivered by one or more fibers such as fiber 32, or by simple optics such as mirrors prisms and lenses.

Fluorescence

Other optical parameters can be acquired by a spectral imaging instrument to identify and analyze materials. The illumination of the target with the OPO beam can induce fluorescence emission at specific wavelengths, which can be imaged as a function of the excitation wavelength.

Wider Wavelength Range

The wavelength range of present spectral imaging instruments is dictated by the emission of the light source and the transmission of the filters. A single OPO system can provide continuous tuning from about 200 nm in the UV to over 2500 nm in the IR.

Other Tunable Light Sources

Although the OPO is the preferred tunable light source, other tunable light sources can be utilized for lower cost systems. These other sources include a combination of a broad band light source such as an incandescent lamp and a spinning filter wheel which transmits light at a number of separate wavelengths, one wavelength at a time; the number corresponding to the number of filters. The light source should generate the light in short pulses to assure that the images of the moving target is not blurred too much and the image quality generated by a single pulse of light will be sufficient to analyze the data. A grating can also be used with a broad band light source to provide a variety of separate wavelengths for illuminating a target region with light at one wavelength at a time.

While the present invention has been described above in terms of specific preferred embodiments, persons skilled in this art will recognize that there are many variations and modifications that could be made. Therefore, the scope of the invention should be determined by the appended claims and not limited by the above descriptions.

What is claimed is:

1. A spectral imaging system for collecting multi-spectral information of a two dimensional target in motion relative to the imaging system, said system comprising:
 A) a pulsed light source tunable in wavelength for producing short pulses of wavelength tuned light at a plurality of selected narrow band wavelengths within a spectral range,
 B) one or more optical components for conveying or directing said short pulses of light to a two dimensional region that is substantially stationary with respect to the imaging system and through which the two dimensional objects are moving relative to the imaging system, and
 C) a camera synchronized with said tunable pulsed light source and comprising a many pixel array detector, said camera being adapted to:
  i) detect light in the selected narrow band wavelengths produced by said tunable pulsed light source and reflected from or transmitted through said two dimensional target in motion relative to the imaging system and passing through a region imaged by the camera, said region or a portion of said region defining a two-dimensional target region and
  ii) provide a plurality of two-dimensional image frames, each frame defining a plurality of two-dimensional pixels within each image frame of said plurality of image frames with each frame at a defined wavelength band,
 D) a processor adapted to process information from said tunable light source and said camera and to produce multi-spectral image cubes of said target from said information, said image cubes identifying a plurality of optical values for each of said two-dimensional pixels of said target passing through the target region;
wherein system parameters are defined as follows:
Np=a number of pixels in the motion direction
Nps=a number of pixels in a the strip's width
Ns=a number of strips in a the field of view
PIX=virtual pixel dimensions
PRR=pulse repletion rate of the laser
V=target speed (conveyor belt speed)
$\Delta\lambda$=a wavelength range
F=number of frames (spectral bands in the spectral data)
SR=spectral resolution
Ws=strip width,
and the system parameters are adjusted such that each strip is exposed only once to each wavelength as it travels across the a target area so the a number of pulses that a strip is exposed to is equal to the number strips in the target area, which is also equal to the number of data points (#F) in the collected spectral data, so:

$$\#F = Ns = \frac{Np}{Nps}$$

and the spectral resolution is equal to a total wavelength range scanned by the tunable laser divided by the number of the collected data points, i.e.

$$SR = \frac{\Delta\lambda}{\#F}$$

and for a desired number of frames #F the required speed V is the product of the pulse repetition rate and the width of the strip, so:

$V = W_s * PRR = N_{ps} * PIX * PRR.$

2. The spectral imaging system as in claim 1 wherein the strip width is as narrow as a single pixel.

3. The spectral imaging system as in claim 1 wherein the strip width is wider than a single pixel.

4. The spectral imaging system as in claim 1 wherein the system is adapted such that a wavelength tuning scans over an entire wavelength range in the same time that it takes for an object to travel across a target area so that the time to complete the scan is provided by the following equation:

$$T = \frac{Np * PIX}{V}.$$

* * * * *